United States Patent
Min et al.

(10) Patent No.: US 11,594,335 B2
(45) Date of Patent: Feb. 28, 2023

(54) AUGMENTED REALITY VIRUS TRANSMISSION RISK DETECTOR

(71) Applicant: Optum, Inc., Minnetonka, MN (US)

(72) Inventors: Geo Min, Raleigh, NC (US); Kassi Elana Dibert, Raleigh, NC (US); Tiffany K. Nguyen, Cary, NC (US); Zachary B. Rosen, Charlotte, NC (US); Samuel Landon Larsen, Raleigh, NC (US)

(73) Assignee: Optum, Inc., Minnetonka, MN (US)

( * ) Notice: Subject to any disclaimer, the term of this patent is extended or adjusted under 35 U.S.C. 154(b) by 161 days.

(21) Appl. No.: 17/197,909

(22) Filed: Mar. 10, 2021

(65) Prior Publication Data

US 2022/0172846 A1 Jun. 2, 2022

Related U.S. Application Data

(60) Provisional application No. 63/120,421, filed on Dec. 2, 2020.

(51) Int. Cl.
*G16H 50/30* (2018.01)
*G16H 50/20* (2018.01)
(Continued)

(52) U.S. Cl.
CPC ............. *G16H 50/30* (2018.01); *G06N 20/00* (2019.01); *G06T 7/0012* (2013.01); *G06T 7/50* (2017.01);
(Continued)

(58) Field of Classification Search
CPC ........ G16H 50/30; G16H 10/60; G16H 15/00; G16H 50/20; G06T 7/50; G06T 7/0012;
(Continued)

(56) References Cited

U.S. PATENT DOCUMENTS

| 8,208,681 B2 | 6/2012 | Heller et al. |
| 9,406,212 B2 | 8/2016 | De Luca et al. |
| 9,695,981 B2 | 7/2017 | Au et al. |
| 10,679,488 B2 | 6/2020 | Liu et al. |
| 10,846,857 B1 | 11/2020 | Graves et al. |

(Continued)

FOREIGN PATENT DOCUMENTS

| WO | 2019/211764 A1 | 11/2019 |
| WO | 2019/236120 A1 | 12/2019 |

OTHER PUBLICATIONS

Agarwal, Rachit et al. "Infection Risk Score: Identifying the Risk of Infection Propagation Based on Human Contact," arXiv:2009.12588v1, Sep. 26, 2020, (9 pages), In Proceedings of the 1st ACM SIGSPATIAL International Workshop on Modeling and Understanding the Spread of COVID-19, Nov. 3, 2018, Seattle, Washington.

(Continued)

*Primary Examiner* — Jin Ge
(74) *Attorney, Agent, or Firm* — Alston & Bird LLP

(57) ABSTRACT

There is a need to accurately and dynamically evaluate an individual's risk associated with the transmission or contraction of a disease. This need can be addressed, for example, by generation of a real-time or near real-time predicted disease score for an associated user. In one example, a method includes receiving a video stream data object depicting a visual representation of a target user; processing the video stream data object to generate a protective covering indication with respect to the target user; processing the video stream data object to generate a spatial proximity determination score with respect to the target user; processing the protective covering indication and spatial proximity determination score to generate a predicted disease score associated with the target user; and providing an augmented reality video stream data object configured to (Continued)

depict the visual representation of the target user and the predicted disease score.

20 Claims, 9 Drawing Sheets

(51) Int. Cl.
| | |
|---|---|
| *G16H 10/60* | (2018.01) |
| *G16H 15/00* | (2018.01) |
| *G06N 20/00* | (2019.01) |
| *G06T 7/00* | (2017.01) |
| *G06T 11/00* | (2006.01) |
| *G06T 7/50* | (2017.01) |
| *G06V 20/40* | (2022.01) |
| *G06V 40/16* | (2022.01) |

(52) U.S. Cl.
CPC ............ *G06T 11/001* (2013.01); *G06V 20/40* (2022.01); *G06V 40/161* (2022.01); *G16H 10/60* (2018.01); *G16H 15/00* (2018.01); *G16H 50/20* (2018.01); *G06T 2207/10016* (2013.01); *G06T 2207/20081* (2013.01); *G06T 2207/30201* (2013.01)

(58) Field of Classification Search
CPC ......... G06T 11/001; G06T 2207/10016; G06T 2207/20081; G06T 2207/30201; G06N 20/00; G06V 40/161
USPC ........................................................ 345/633
See application file for complete search history.

(56) References Cited

U.S. PATENT DOCUMENTS

| | | | | |
|---|---|---|---|---|
| 2016/0300252 | A1* | 10/2016 | Frank | ................ G06F 16/24578 |
| 2018/0285630 | A1* | 10/2018 | Han | ...................... G06V 40/172 |
| 2021/0216773 | A1* | 7/2021 | Bohannon | .............. G06V 20/20 |

OTHER PUBLICATIONS

Gorordo, Ibai. "Part 2-Yet Another Face Mask Detector . . . (OpenCV Spatial Al Competition Journey)," Towards Data Science, Aug. 24, 2020, (10 pages), [article, online]. [Retrieved from the Internet Mar. 24, 2021] <URL:https://towardsdatascience.com/part-2-yet-another-face-mask-detector-opencv-spatial-ai-competition-journey-91dfaf96c6e8>.

Rosebrock, Adrian. "COVID-19: Face Mask Detector With OpenCV, Keras/TensorFlow, and Deep Learning," PyImageSearch, May 4, 2020, (49 pages), [article, online]. [Retrieved from the Internet Mar. 22, 2021] <URL:https://www.pyimagesearch.com/2020/05/04/covid-19-face-mask-detector-with-opencv-keras-tensorflow-and-deep-earning/>.

Yadav, Shashi. "Deep Learning Based Safe Social Distancing and Face Mask Detection in Public Areas For COVID-19 Safety Guidelines Adherence," International Journal For Research in Applied Science & Engineering Technology (IJRASET), vol. 8, Issue VII, Jul. 2020, pp. 1368-1375. ISSN: 2321-9653, IC Value: 45.98, SJ Impact Factor: 7.429.

* cited by examiner

400

Receive a video stream data object comprising sequential image data generated by a video capture device and depicting a visual representation of a target user
402

Generate a protective covering indication using a covering detection machine learning model
404

Generate a spatial proximity determination score using a spatial proximity machine learning model
406

Generate a predicted disease score using a logarithmic merger machine learning model
408

Provide an augmented reality video stream data object
410

FIG. 4

Receive a video stream data object depicting a visual representation of a target user
602
Generate an age prediction using an age estimation machine learning model
604
Update the predicted disease score using the logarithmic merger machine learning model
606
FIG. 6

408C

```
Receive a video stream data object depicting a visual representation of a
target user
702
```

```
Generate an illness observation indication using an illness detection
machine learning model
704
```

```
Update the predicted disease score using a logarithmic merger machine
learning model
706
```

Receive a video stream data object depicting a visual representation of a target user
802
Generate an environmental risk determination score using an environmental monitoring machine learning model
804
Update the predicted disease score using a logarithmic merger machine learning model
806
FIG. 8

AUGMENTED REALITY VIRUS TRANSMISSION RISK DETECTOR

CROSS-REFERENCES TO RELATED APPLICATION(S)

The present application claims priority to U.S. Provisional Patent Application No. 63/120,421 (filed Dec. 2, 2020), which is incorporated herein by reference in its entirety.

BACKGROUND

Various embodiments of the present invention address technical challenges related to accurately and dynamically evaluating risk scores based at least in part on video data.

BRIEF SUMMARY

In general, embodiments of the present invention provide methods, apparatuses, systems, computing devices, computing entities, and/or the like for dynamically generating a predicted disease score for a video stream data object depicting a visual representation of a target user.

In accordance with one aspect, a method includes: receiving, using one or more processors, a video stream data object, wherein the video stream data object comprises (a) sequential image data generated by a video capture device, and (b) depicts a visual representation of a target user; generating, using the one or more processors and by utilizing a covering detection machine learning model, a protective covering indication with respect to the visual representation of the target user depicted in the video stream data object, wherein the covering detection machine learning model is configured to process at least the video stream data object to generate the protective covering indication; generating, using the one or more processors and by utilizing a spatial proximity machine learning model, a spatial proximity determination score with respect to the visual representation of the target user depicted in the video stream data object and the video capture device, wherein the spatial proximity machine learning model is configured to process at least the video stream data object to generate the spatial proximity determination score; generating, using the one or more processors and by utilizing a logarithmic merger machine learning model, a predicted disease score, wherein the logarithmic merger machine learning model is configured to process at least the protective covering indication and spatial proximity determination score to generate the predicted disease score; and generating and providing an augmented reality video stream data object for presentation to an end user, wherein the augmented reality video stream data object comprises (a) the visual representation of the target user, and (b) the predicted disease score.

In accordance with another aspect, an apparatus comprising at least one processor and at least one memory including program code, the at least one memory and the program code configured to, with the processor, cause the apparatus to at least: receive a video stream data object, wherein the video stream data object comprises (a) sequential image data generated by a video capture device, and (b) depicts a visual representation of a target user; generate, using a covering detection machine learning model, a protective covering indication with respect to the visual representation of the target user depicted in the video stream data object, wherein the covering detection machine learning model is configured to process at least the video stream data object to generate the protective covering indication; generate, using a spatial proximity machine learning model, a spatial proximity determination score with respect to the visual representation of the target user depicted in the video stream data object and the video capture device, wherein the spatial proximity machine learning model is configured to process at least the video stream data object to generate the spatial proximity determination score; generate, using a logarithmic merger machine learning model, a predicted disease score, wherein the logarithmic merger machine learning model is configured to process at least the protective covering indication and spatial proximity determination score to generate the predicted disease score; and provide an augmented reality video stream data object for presentation to an end user, wherein the augmented reality video stream data object comprises (a) the visual representation of the target user, and (b) the predicted disease score.

In accordance with yet another aspect, a computer program product computer program comprising at least one non-transitory computer-readable storage medium having computer-readable program code portions stored therein, the computer-readable program code portions configured to: receive a video stream data object, wherein the video stream data object comprises (a) sequential image data generated by a video capture device, and (b) depicts a visual representation of a target user; generate, using a covering detection machine learning model, a protective covering indication with respect to the visual representation of the target user depicted in the video stream data object, wherein the covering detection machine learning model is configured to process at least the video stream data object to generate the protective covering indication; generate, using a spatial proximity machine learning model, a spatial proximity determination score with respect to the visual representation of the target user depicted in the video stream data object and the video capture device, wherein the spatial proximity machine learning model is configured to process at least the video stream data object to generate the spatial proximity determination score; generate, using a logarithmic merger machine learning model, a predicted disease score, wherein the logarithmic merger machine learning model is configured to process at least the protective covering indication and spatial proximity determination score to generate the predicted disease score; and provide an augmented reality video stream data object for presentation to an end user, wherein the augmented reality video stream data object comprises (a) the visual representation of the target user, and (b) the predicted disease score.

BRIEF DESCRIPTION OF THE DRAWINGS

Figure 1:
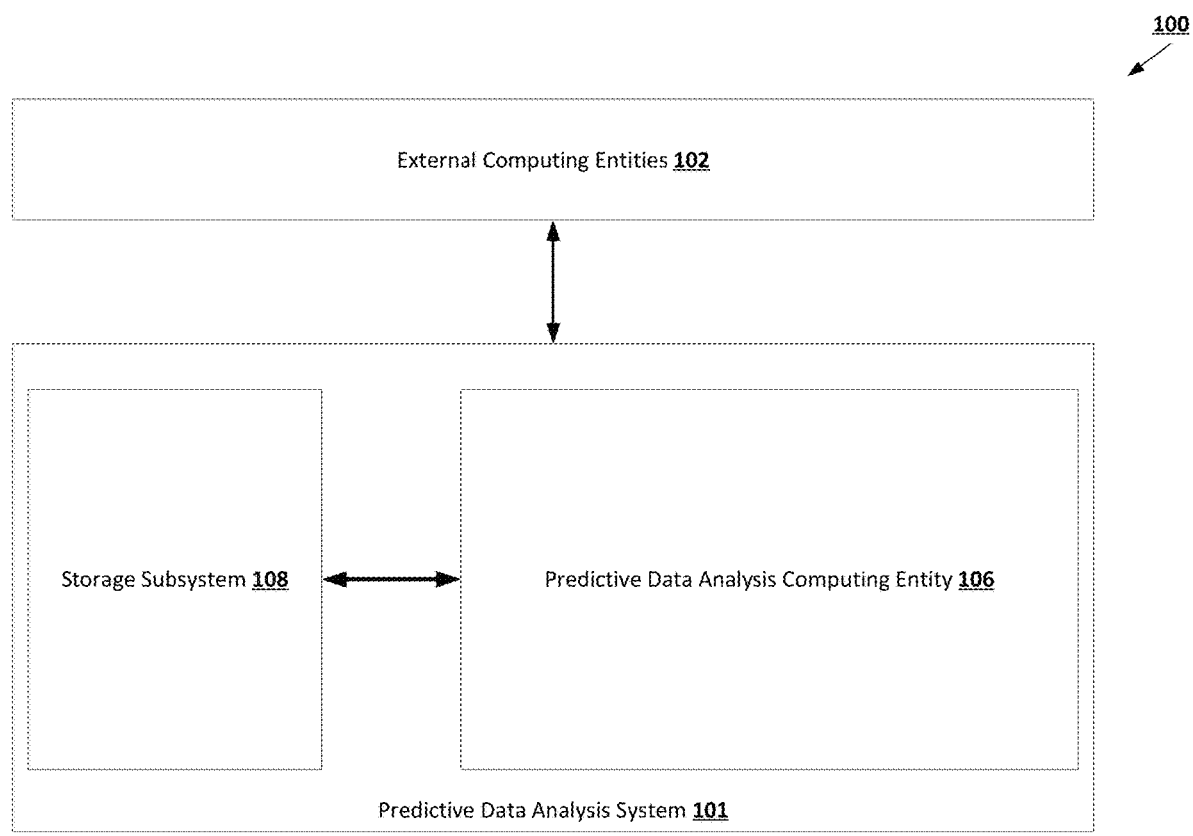
Figure 2:
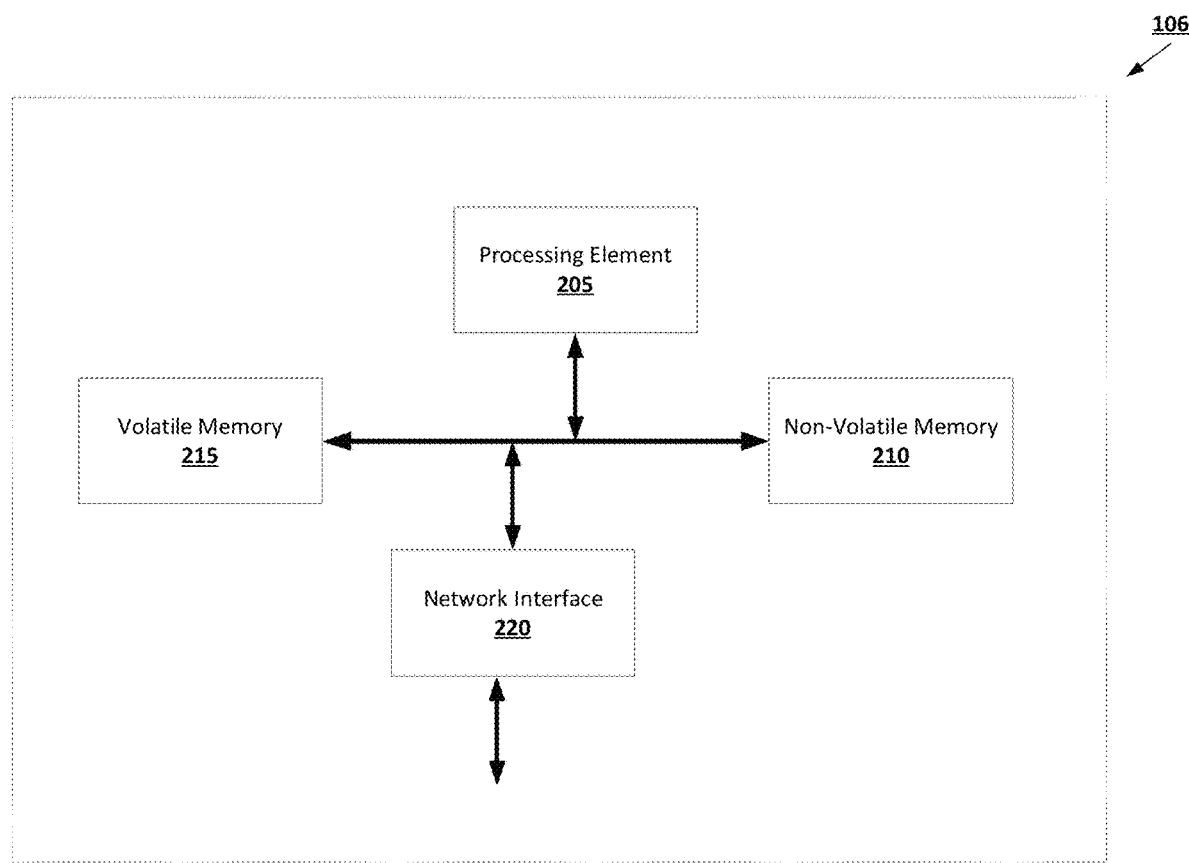
Figure 3:
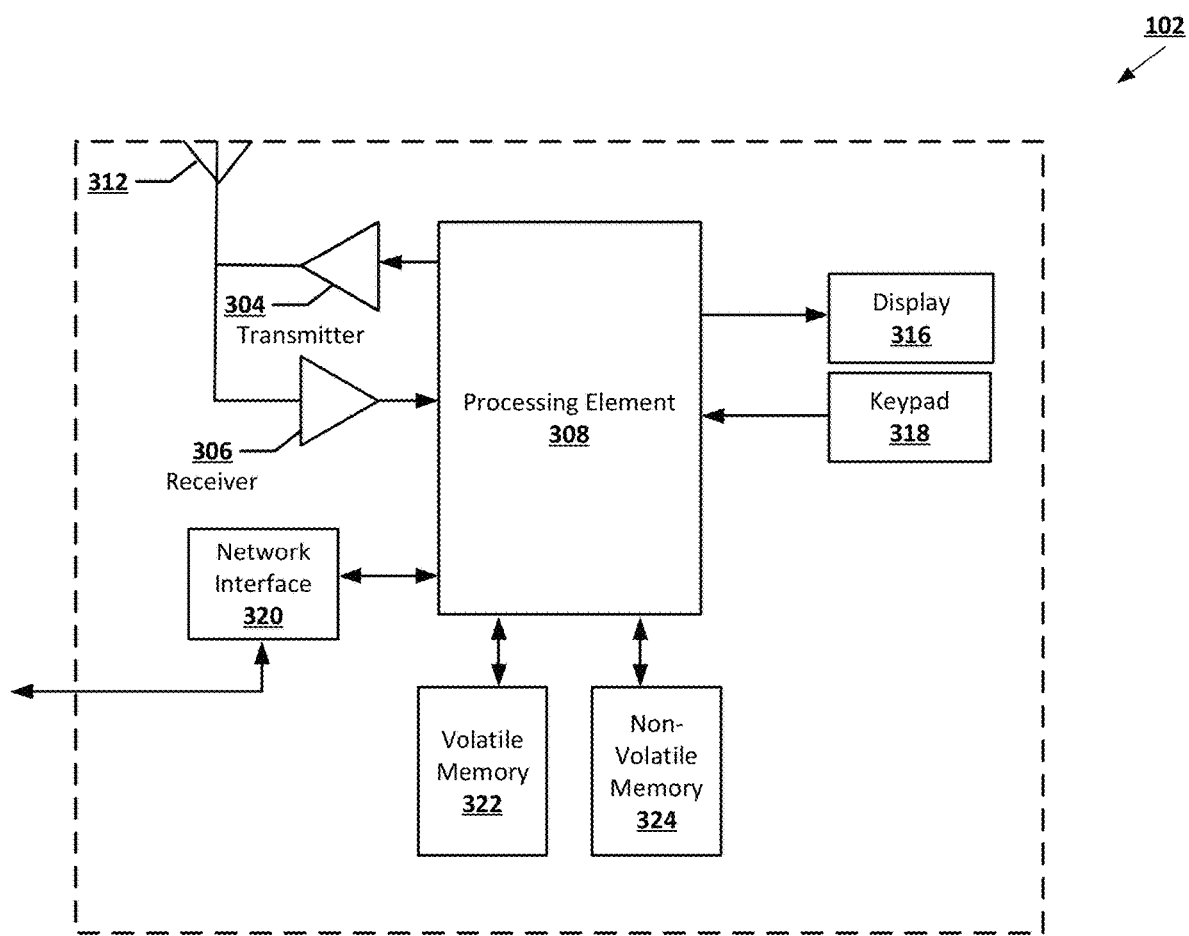
Figure 5:
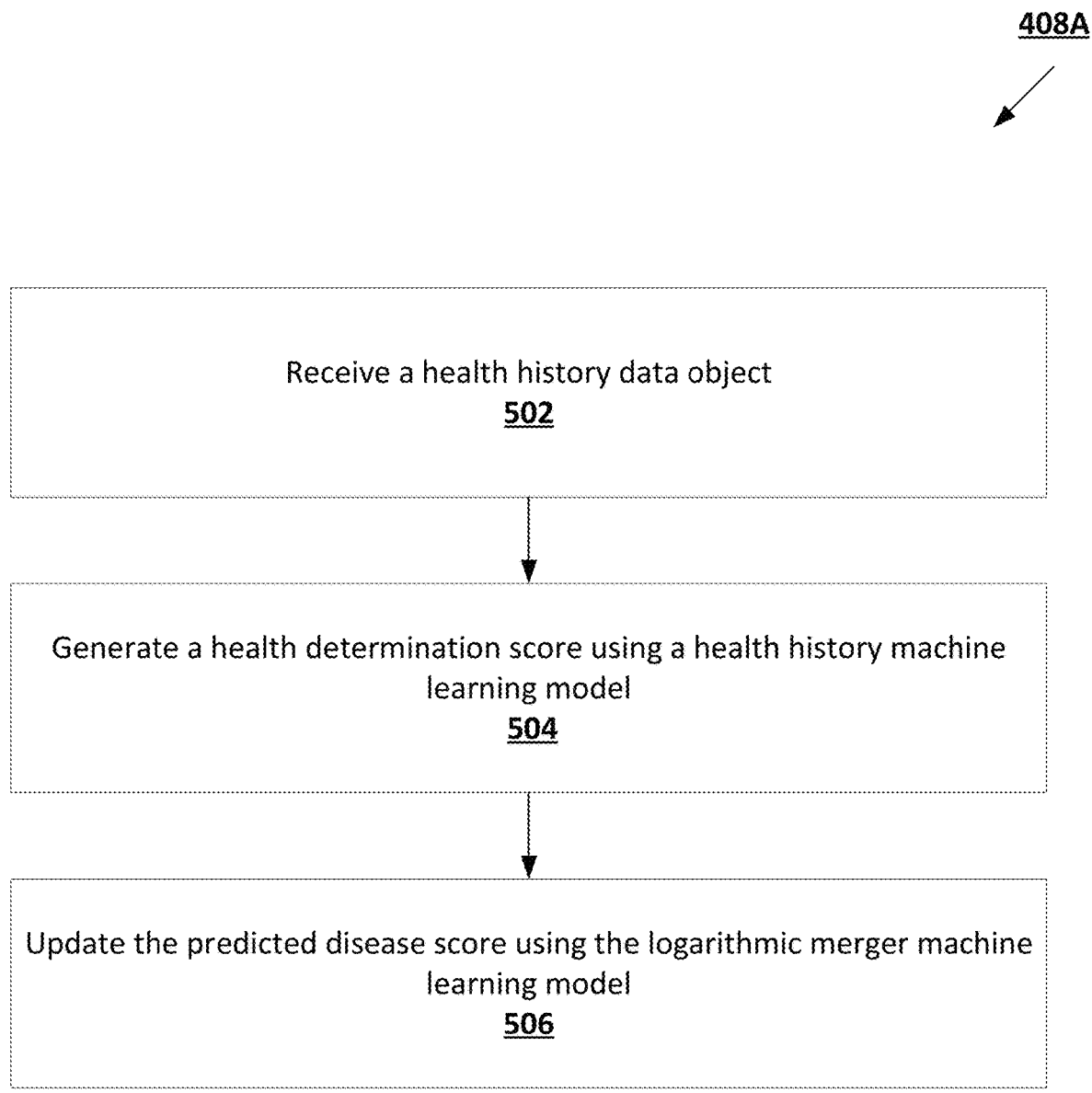
Figure 7:
Figure 9A:
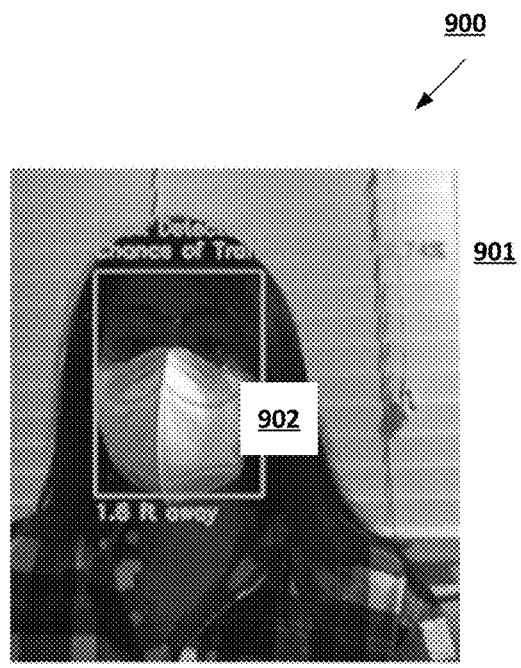

Having thus described the invention in general terms, reference will now be made to the accompanying drawings, which are not necessarily drawn to scale, and wherein:

FIG. 1 provides an exemplary overview of a system that can be used to practice embodiments of the present invention;

FIG. 2 provides an example predictive data analysis computing entity in accordance with some embodiments discussed herein;

FIG. 3 provides an example external computing entity in accordance with some embodiments discussed herein;

FIG. 4 provides a flowchart diagram of an example process for generating a predicted disease score for a target user depicted in a video stream data object in accordance with some embodiments discussed herein;

FIG. 5 provides a flowchart diagram of an example process for updating a predicted disease score based at least in part on a health history data object in accordance with some embodiments discussed herein;

FIG. 6 provides a flowchart diagram of an example process for updating a predicted disease score based at least in part on an age prediction in accordance with some embodiments discussed herein;

FIG. 7 provides a flowchart diagram of an example process for updating a predicted disease score based at least in part on an illness observation indication in accordance with some embodiments discussed herein;

FIG. 8 provides a flowchart diagram of an example process for updating a predicted disease score based at least in part on an environmental risk determination score in accordance with some embodiments discussed herein; and FIGS. 9A and B provides operational examples of two augmented reality video stream data object outputs in accordance with some embodiments discussed herein.

DETAILED DESCRIPTION

Various embodiments of the present invention are described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW AND TECHNICAL ADVANTAGES

Various embodiments of the present invention address technical challenges related to accurately and dynamically evaluating an individual's risk associated with the transmission or contraction of a disease. Although certain health and safety protocols (such as maintaining a certain distance from other individuals or wearing a protective face covering) may reduce the likelihood that a disease is transmitted or contracted by an individual, these health and safety protocols are simply precautions that an individual may adhere to but provide no real indication of an up-to-date risk assessment for the individual. While certain software models are capable of determining whether such precautions are followed, these models do not provide an indication of an up-to-date risk assessment for individuals. Further, such models do not consider the health of the individual or the individual's surrounding environment, which may also play a role when determining an individual's risk. Additionally, these models may not be performed in real-time, thereby not reflecting the most current actions of the individual.

To address the above-noted technical challenges associated with accurately and dynamically evaluating disease transmission and contraction, various embodiments of the present invention describe a logarithmic merger machine learning model configured to generate a predicted disease score associated with a target user. The predicted disease score may be generated in real-time or near real-time such that the impact of the target user's current actions is reflected in the predicted disease score. The logarithmic merger machine learning model may receive input from a covering detection machine learning model and a spatial proximity machine learning model configured to generate a protective covering indication and spatial proximity determination score, respectively. Using these inputs, the logarithmic merger machine learning model may in some embodiments, be able to generate a predicted disease score for the individual that is indicative of a real-time, up-to-date risk assessment for transmitting or contracting a disease. In some embodiments, the logarithmic merger machine learning model may be also be configured to receive input from at least one of health history machine learning model, an age determination machine learning model, an illness detection machine learning model, and an environmental machine learning model. In some embodiments, with the inclusion of any one or more of the additional models, the logarithmic merger machine learning model can provide a more tailored and customized predicted disease score that takes into account one or more additional inputs such as the individual's age, one or more medical conditions, or environmental surroundings.

Importantly, the use of separate machine learning models to generate different outputs allows for a modulated predicted disease score system. That is, by using more than one model, these multiple models produce various outputs that may be generated simultaneously. This allows the system to reflect the most up-to-date predicted disease score for an associated individual in real-time, such that actions an associated individual may take are reflected in their associated real time, up-to-date predicted disease score. Additionally, the noted various modularized system may accomplish these objectives while reducing the computational complexity of the runtime operations that need to be performed by using multiple models to generate such outputs. This results in a more time efficient and less computationally resource-intensive method to generate an up-to-date predicted disease score for the target user.

II. DEFINITIONS OF CERTAIN TERMS

The term "video stream data object" may refer to an electronically received data construct that is configured to describe sequential image data generated by a video capture device depicting a visual representation of a target user. The video stream data object may also describe audiovisual data (i.e., audio data, visual data, or both audio data and visual data) pertaining to the target user as well as any additional audiovisual data not directly pertaining to the target user. In some embodiments, the video stream data object depicting a visual representation of a target user may be processed to determine an associated predicted disease score for the target user depicted in the video stream data object.

The term "augmented reality video stream data object" may refer to an electronically managed data construct that describes audiovisual data received from the video stream data object along with one or more embedded augmented reality user interface elements, where the augmented reality video stream data object is configured to be presented to at least a target user via a display screen. In an example context, the augmented reality video stream data object comprises a visual representation of a target user and a predicted disease score associated with the visual representation of the target user as determined by a logarithmic merger machine learning model. In some embodiments, the augmented reality video stream data object also comprises an embedded bounding box element. With the embedded bounding box element, the augmented reality video stream data object further comprises a color-coded bounding box centered about the visual representation of the target user's face, where the color of the color-coded bounded box may indicate whether the predicted disease score for the visual representation of the target user satisfiers or fails to satisfy (e.g., is above or below) a predefined predicted disease score threshold. In some embodiments, the augmented reality video stream data object may comprise an embedded recommendation element, where the recommendation element displays one or more recommended actions the target user depicted by the video stream data object may take to reduce their associated predicted disease score.

The term "video capture device" may refer to any electronic device configured with a camera and capable of electronically transmitting video stream data objects. Example video capture devices may include a smartphone, webcam, tablet computer, laptop computer, wearable device (e.g. smart glasses, smartwatch, and/or the like), digital signage, and/or the like. In some embodiments, the video capture device may also be configured to display the augmented reality video stream data object on its associated display screen for viewing by at least the target user. In some embodiments, the apparatus comprising the display screen is separate from the video capture device.

The term "target user" may refer to an individual that is within the field of view of the video capture device such that a visual representation of individual is captured in the video stream data object. The video stream data object may capture the visual representation of the target user and the visual representation depicting the target user may be used in various machine learning models discussed hereinbelow. In some embodiments, in instances where there is more than one individual in view of the video capture device, the visual representation of a target user refers to the visual representation of the individual positioned closest to the video capture device. In some embodiments, the term target user may refer to more than one individual whose visual representation is depicted in the video stream data object. For example, a target user may comprise any individual whose visual representation is depicted in the video stream data object.

The term "covering detection machine learning model" may refer to an electronically-stored data construct that is configured to describe parameters, hyper-parameters, and/or stored operations of a machine learning model that is configured to process a video stream data object in order to generate a protective covering indication. In some embodiments, the covering detection machine learning model is a trained machine learning model (e.g., a trained convolutional neural network machine learning model) that is configured to process a visual representation of a target user depicted in the video stream data object in order to generate the protective covering indication. In some embodiments, the covering detection machine learning model may be a classification machine learning model. For example, a corresponding covering detection machine learning model may be trained using observed data about whether a visual representation of a target user is wearing a protective face covering, e.g. a face mask or the like. In some embodiments, the covering detection machine learning model may be trained to determine if a visual representation of a target user is detected to be correctly wearing a protective face covering. In some embodiments, the parameters/hyper-parameters of a covering detection machine learning model may be represented as binary values in a two-dimensional array, such as a matrix.

The term "spatial proximity machine learning model" may refer to an electronically-stored data construct that is configured to describe parameters, hyper-parameters, and/or stored operations of a machine learning model that is configured to process a video stream data object in order to generate a spatial proximity determination score. In some embodiments, the spatial proximity machine learning model is a trained machine learning model that is configured to process a visual representation of a target user depicted in the video stream data object in order to generate the spatial proximity determination score. The spatial proximity machine learning model may be a trained machine learning model (e.g., a trained convolutional neural network machine learning model) may be configured to process one or more measures of an estimated number of pixels comprising the visual representation of the target user face. Based at least in part on the estimated number of pixels comprising the visual representation of the target user's face, a predefined face length, and a focal length of the video capture device, the spatial proximity machine learning model may generate a spatial proximity determination score. In some embodiments, the spatial proximity determination score is an estimation of the distance between the target user depicted in the video stream data object and the video capture device. In some embodiments, the spatial proximity machine learning model is a regression machine learning model. The parameters/hyper-parameters of a spatial proximity machine learning model may be represented as a one-dimensional array.

The term "health history machine learning model" may refer to an electronically-stored data construct that is configured to describe parameters, hyper-parameters, and/or stored operations of a machine learning model that is configured to process a health history data object in order to generate a health determination score. In some embodiments, the health history machine learning model is a trained machine learning model that is configured to process a health history data object pertaining to the health history of a target user depicted in a video stream data object in order to generate a health determination score associated with the depicted target user. For example, the health history machine learning model is a trained machine learning model (e.g., a neural network machine learning model) that may include a feature engineering layer that is configured to process the health history data object to infer features related to at least the age, gender, and one or more associated medical conditions for the target user depicted in the video stream data object. In some embodiments, a determined age may be represented as a numeric feature, gender may be represented as a one hot encoded value, and the health status and associated medical conditions may be represented as categorical values. Such medical condition categories may include a high risk category, a medium risk category, and/or a low risk category, where high risk category indicates that the target user depicted in the video stream data object has one or more medical conditions known to increase their associated risk of severe illness should the disease be contracted, and the medium risk category indicates that the target user depicted in the video stream data object has one or more medical conditions that may increase their associated risk of severe illness should the disease be contracted. The high risk and medium risk categories may each be associated with a set of predefined associated medical conditions. For example, the high risk category may include medical conditions such as cancer, kidney disease, heart conditions, chronic obstructive pulmonary disease, organ transplant, obese, pregnant, nursing, sickle cell disease, smoking, and type 2 diabetes. The medium risk category may include medical conditions such as asthma, cerebrovascular disease, cystic fibrosis, hypertension, weakened immune system, dementia, liver disease, overweight, pulmonary fibrosis, thalassemia, or type 1 diabetes. The health history machine learning model may determine if the target user depicted in the video stream data object has one or more of the associated health conditions listed in the either the high risk category or medium risk category. If no associated health conditions are determined to be listed in the high risk category or medium risk category, the health history machine learning model may determine that the target user depicted in the video stream data object is in the low risk category. In some embodiments, the health history machine learning model is a natural language processing machine learning model. The parameters/hyper-parameters of the health history machine learning model may be represented as a two-dimensional array, such as a matrix.

The term "age estimation machine learning model" may refer to an electronically-stored data construct that is configured to process a video stream data object in order to generate an age prediction. In some embodiments, the age estimation machine learning model is a trained machine learning model that is configured to process a visual representation of a target user depicted in the video stream data object in order to generate the age estimation determination score. The age estimation machine learning model may be able to determine an age category for a target user depicted in the video stream data object. For example, the age estimation machine learning model may determine that the target user depicted in the video stream data object is between 30-39 years old. As another example, the age estimation machine learning model may determine the user is over 85 years old. In some embodiments, the age estimation machine learning model may be configured to assign the target user an age category amongst a set of predetermined age ranges. In some embodiments, the age estimation machine learning model is a classification model. The parameters/hyper-parameters of a spatial proximity machine learning model may be represented as a two-dimensional array, such as a matrix.

The term "illness detection machine learning model" may refer to an electronically-stored data construct that is configured to process a video stream data object in order to generate an illness observation indication. In some embodiments, the illness detection machine learning model is a trained machine learning model that is configured to process a visual representation of a target user depicted in the video stream data object in order to generate the illness observation indication. In some embodiments, the illness detection machine learning model may be trained to recognize one or more visual illness patterns. For example, the illness detection machine learning model may be trained to detect visual illness patterns such as user gestures related to sneezing, coughing, or the like. In some embodiments, the illness detection machine learning model may be configured to detect auditory illness patterns. For example, the illness detection machine learning model may be configured to detect auditory illness patterns produced when a target user sneezes or coughs. In some embodiments, the illness detection machine learning model is a classification model. The parameters/hyper-parameters of an illness detection machine learning model may be represented as binary values in a one-dimensional array.

The term "environmental monitoring machine learning model" may refer to an electronically-stored data construct that is configured to process a video stream data object in order to generate an environmental risk determination score. In some embodiments, the environmental monitoring machine learning model is a trained machine learning model that is configured to process a visual representation of an environment of a target user depicted in the video stream data object in order to generate the environmental risk determination score. A corresponding environmental monitoring machine learning model may be trained using observed data regarding the environment of a target user. For example, observed data about the environment of a target user depicted in the video stream data object may include the number of other individuals depicted by the video stream data object, a detected distance between the visual representations of the other individuals and visual representation of the target user, and a location of a target user. In some embodiments, the environmental monitoring machine learning model includes both a regression model portion and a classification model portion. The parameters/hyper-parameters of a spatial proximity machine learning model may be represented as a two-dimensional array, such as a matrix.

The term "logarithmic merger machine learning model" may refer to an electronically-stored data construct that is configured to describe parameters, hyper-parameters, and/or stored operations of a machine learning model that is configured to process at least a protective covering indication and a spatial proximity determination score in order to generate a predicted disease score for a visual representation of a target user depicted in a video stream data object. In some embodiments, the logarithmic merger machine learning model may be configured to process one or more additional inputs, such as a health determination score from a health history machine learning model, an age prediction from an age estimation machine learning model, and/or an environmental risk determination score from an environmental monitoring machine learning model. The parameters/hyper-parameters of a logarithmic merger machine learning model may be represented as a two-dimensional array, such as a matrix. In some embodiments, the generated predicted disease score may be represented as a percentage.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware framework and/or operating system platform. A software component comprising assembly language instructions may require conversion into executable machine code by an assembler prior to execution by the hardware framework and/or platform. Another example programming language may be a higher-level programming language that may be portable across multiple frameworks. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatuses, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM FRAMEWORK

FIG. 1 is a schematic diagram of an example system architecture 100 for performing predictive data analysis operations and for performing one or more prediction-based actions (e.g., generating corresponding user interface data). The system architecture 100 includes a predictive data analysis system 101 comprising a predictive data analysis computing entity 106 configured to generate predictive outputs that can be used to perform one or more prediction-based actions. The predictive data analysis system 101 may communicate with one or more external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like). An example of a prediction that may be generated by using the system architecture 100 is to a generate predicted disease score associated with a target user depicted in a video stream data object.

The system architecture 100 includes a storage subsystem 108 configured to store at least a portion of the data utilized by the predictive data analysis system 101. The predictive data analysis computing entity 106 may be in communication with one or more external computing entities 102. The predictive data analysis computing entity 106 may be configured to receive requests and/or data from external computing entities 102, process the requests and/or data to generate predictive outputs (e.g., predictive data analysis data objects), and provide the predictive outputs to the external computing entities 102. The external computing entity 102 (e.g., a video capture device) may periodically update/provide raw input data (e.g., video stream data objects depicting a target user) to the predictive data analysis system 101. The external computing entities 102 may further generate user interface data (e.g., one or more data objects) corresponding to the predictive outputs and may provide (e.g., transmit, send and/or the like) the user interface data corresponding with the predictive outputs for presentation to user computing entities operated by end-users.

The storage subsystem 108 may be configured to store at least a portion of the data utilized by the predictive data analysis computing entity 106 to perform predictive data analysis steps/operations and tasks. The storage subsystem 108 may be configured to store at least a portion of operational data and/or operational configuration data including operational instructions and parameters utilized by the predictive data analysis computing entity 106 to perform predictive data analysis steps/operations in response to requests. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. Such functions, steps/operations, and/or processes may include, for example, transmitting, receiving, operating on, processing, displaying, storing, determining, creating/generating, monitoring, evaluating, comparing, and/or similar terms used herein interchangeably. In one embodiment, these functions, steps/operations, and/or processes can be performed on data, content, information, and/or similar terms used herein interchangeably.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with a processing element 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include at least one non-volatile memory 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include at least one volatile memory 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these frameworks and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a video capture device (e.g., camera), a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

To address the technical challenges associated with performing accurately and dynamically evaluating the risk associated with the transmission or contraction of a disease for a visual representation of target user depicted in a video stream data object, various embodiments of the present invention describe a logarithmic merger machine learning model configured to generate predicted disease score for the target user depicted in the video stream data object using various inputs from other machine learning models. Because the logarithmic merger machine learning model takes input from other machine learning models, the logarithmic merger machine learning model avoids the runtime efficiency issues of various existing machine learning models and thus improve the speed of performing an accurate and dynamic risk evaluation for a target user depicted in the video stream data object in a real-time or near-real-time manner.

FIG. 4 is a flowchart diagram of an example process 400 for predictive disease scoring associated with a visual representation of a target user depicted in a video stream data object. Via the various steps/operations of the process 400, the predictive data analysis computing entity 106 can accurately and dynamically generate a real-time personalized predicted disease score associated with a target user depicted in a video stream data object and provide said predicted disease score to the target user via an external computing entity 102.

The process 400 begins at step/operation 402 when the predictive data analysis computing entity 106 receives a video stream data object depicting a visual representation of a target user. The video stream data object may be received from an external device, such as a video capture device capable of electronically transmitting the video stream data object. In some embodiments, the video stream data object describes data associated with a livestream that is recorded and transmitted by the video capture device simultaneously, such that the predictive data analysis computing entity 106 receives the video stream data object in real-time or in near real-time.

The video stream data object may refer to an electronically received data construct that is configured to described sequential image data generated by a video capture device and depicts a visual representation of a target user. The video stream data object may describe audiovisual data associated with the target user as well any audiovisual data not associated with the target user, such as audiovisual data associated with the target user's surrounding environment. In some embodiments, a single individual is chosen as the target user and the visual representation of said target user is analyzed in accordance with example embodiments described hereinbelow. For example, the target user may be the individual closest to the video capture device and whose corresponding visual representation is the largest. In some embodiments, multiple users are chosen as the target user and the visual representation of each user is analyzed in accordance with the example embodiments described hereinbelow.

At step/operation 404, the predictive data analysis computing entity 106 processes the video stream data object using a covering detection machine learning model in order to generate a protective covering indication. A covering detection machine learning model may describe a machine learning model configured to process a visual representation of a target user depicted in the received video stream data object to generate a protective covering score. In some embodiments, the covering detection machine learning model may be trained using observed data to determine whether the visual representation of the target user is wearing a protective face covering. In some embodiments, the covering detection machine learning model is a classification model configured to determine if the visual representation of the target user is wearing a protective covering. For example, if the visual representation of the target user is wearing a mask, the covering detection machine learning model would classify the target user as having a protective covering. By way of continuing example, if the visual representation of the target user is classified as having a protective covering, the covering protection indication may be 1.

In some embodiments, the covering detection machine learning model may be further configured to determine if the visual representation of the target user is correctly wearing a protective face covering. If the covering detection machine learning model determines the visual representation of the target user is not correctly wearing a protective face covering, the covering detection machine learning model may classify the visual representation of the target user as not wearing a protective face covering and reflect this in the protective covering indication. For example, if the visual representation of the target user is wearing a face mask but this mask does not cover the target user's nose, the covering detection machine learning model may classify the visual representation of the target user as not wearing a protective face covering and generate a protective covering indication of 0.

In some embodiments, the inputs to the covering detection machine learning model include the visual representation that may be a collection of one or more matrices, where each matrix represents color values for a set of pixels corresponding to a state of an environment of the target user during a corresponding unit of time. In some embodiments, the output of the covering detection machine learning model is a protective covering score is an atomic value.

At step/operation 406, the predictive data analysis computing entity 106 processes the video stream data object using a spatial proximity machine learning model in order to generate a spatial proximity determination score. A spatial proximity machine learning model may describe a machine learning model configured to process a visual representation of a target user depicted in the received video stream data object to generate a spatial proximity determination score. In some embodiments, the spatial proximity machine learning model may be trained to process one or more measures of an estimated number of pixels comprising the visual representation of the target user's face. The spatial proximity machine learning model may be configured with a predefined face length representative of the length of a human face and receive the focal length of the associated video capture device. Based at least in part on the estimated number of pixels comprising the visual representation of the target user's face, a predefined face length, and a focal length of the associated video capture device, the spatial proximity machine learning model may generate a spatial proximity determination score. In some embodiments, the spatial proximity machine learning model is a regression machine learning model.

In some embodiments, the spatial proximity determination score is an estimation of the distance between the target user depicted in a video stream data object and the video capture device. For example, if a target user is two feet away from the video capture device, the visual representation of the face of the target user depicted in the video stream data object would comprise an estimated X number of pixels. In some embodiments, using a predefined face length value, which may be indicative of the average human face length, and a focal length of the video capture device, which may depend on the known specifications of the video capture device, may allow the spatial proximity machine learning model to generate a spatial proximity determination score to estimate the distance between the target user depicted in the video stream data object and the video capture device. In another example, using the same video capture device, if the same target user is now six feet away from the video capture device, the visual representation of the face of the target user may now comprise an estimated Y number of pixels, where Y number of pixels is less than X number of pixels due to the target user being positioned further from the video capture device than in the first scenario. The spatial proximity machine learning may estimate a new distance between the target user depicted in the video stream data object and the video capture device and generate a spatial proximity determination score, where the newly generated spatial proximity score estimates a greater distance between the target user depicted in the video stream data object and the video capture device.

In some embodiments, the inputs to the spatial proximity machine learning model include the visual representation that may be a collection of one or more matrices, where each matrix represents color values for a set of pixels corresponding to a state of an environment of the target user during a corresponding unit of time. In some embodiments, the output of the spatial proximity machine learning model is a spatial proximity determination score is an atomic value.

At step/operation 408, the predictive data analysis computing entity 106 processes the protective covering indication as generated by the covering detection machine learning model and the spatial proximity determination score as generated by the spatial proximity machine learning model using a logarithmic merger machine learning model to generate a predicted disease score. A logarithmic merger machine learning model may describe a machine learning model configured to process a protective covering indication as generated by the covering detection machine learning model and the spatial proximity determination score as generated by the spatial proximity machine learning model to generate a predicted disease score associated with the target user depicted in the video stream data object. For example, a covering detection indication of 1 may indicate the visual representation of a target user was determined to be wearing a protective covering and a spatial proximity determination score of 5 may indicate the target user depicted in the video stream data object is five feet away from the video capture device. The logarithmic merger machine learning model may then calculate a predicted disease score based off the covering detection indication and the spatial proximity determination score.

In some embodiments, the logarithmic merger machine learning model uses the value of the spatial distance determination score in a logarithmic algorithm to generate a predicted disease score. In some embodiments, when a visual representation of a target user is processed to determine that the target user is not wearing a protective covering, a predetermined value is added to the predicted disease score generated using the spatial distance determination score logarithmic algorithm. For example, in instances when the visual representation of the target user is determined to be five feet away, the logarithmic merger machine learning algorithm may calculate a predicted disease score. Additionally, if the visual representation of the target user is processed to determine that the target user is not wearing a protective covering, this results in a 30 percentage points added onto the predicted disease score. These operations may be processed in any order or performed simultaneously.

The logarithmic merger machine learning model may be further configured to determine a threshold predicted disease score. The threshold predicted disease score may have a threshold value that is configured to determine whether the transmission/contraction disease risk associated with a target user is excessive, e.g., in a manner such that any predicted disease score value greater than the threshold predicted disease score indicates the target user associated with the predicted disease score value is at increased risk for transmission/contraction of a disease. For example, a predicted disease score of 30% may be chosen as the threshold predicted disease score. In some embodiments, this predicted disease score threshold may be dynamic, such that it varies in accordance with various inputs provided to the logarithmic merger machine learning model. For example, if an indication of a user's health or age is provided to the logarithmic merger machine learning model, as will be discussed below in accordance with some example embodiments below, the threshold predicted disease score may be adjusted accordingly.

In some embodiments, the logarithmic merger machine learning model may be further configured to generate one or more recommended actions for the target user depicted in the video stream data object. A recommended action describes an action the target user depicted in the video stream data object may take to reduce their predicted disease score. The one or more recommended actions may be determined based at least in part on the protective covering indication and the spatial proximity determination score. For example, if the protective covering indication indicates the target user depicted in the video stream data object is not wearing a face covering, logarithmic merger machine learning model may generate a recommended action recommending the user puts a face covering on. As another example, if the spatial proximity determination score indicates the target user depicted in the video stream data object is closer than six feet, the logarithmic merger machine learning model may generate a recommended action recommending the target user moves further away from the video capture device.

In some embodiments, the inputs to the logarithmic merger machine learning model include a vector including at least the protective covering score and the spatial proximity determination score. In some embodiments, the output of the logarithmic merger machine learning model is a predicted disease score is an atomic value.

In some embodiments, step/operation 408 can be performed in accordance with the process 408A that is depicted in FIG. 5. The process 408A that is depicted in FIG. 5 begins at step/operation 502 when the predictive data analysis computing entity 106 receives one or more health history data objects pertaining to the target user and/or the visual representation of the target user. In some embodiments, the one or more health history data objects are a compilation of medical records pertaining to the target user depicted in the video stream data object. In some embodiments, facial recognition software (e.g., TensorFlow facial recognition software) may be used to identify the target user depicted in the video stream data object. Once identified, the target user's medical records may be accessed and a compiled to form the one or more health history data objects. In some embodiments, the one or more health history data objects may be supplied by the target user via an external computing entity 102. For example, a target user may answer a questionnaire indicting their overall health, age, associated diseases, health status, or the like. The one or more health history data objects may be associated a user stored in storage subsystem 108. The predictive data analysis computing entity 106 may access the health history data object associated with the target user depicted in the video stream data object via the storage subsystem 108.

At step/operation 504, the predictive data analysis computing entity 106 processes the one or more health history data objects using a health history machine learning model in order to generate a health determination score. A health history machine learning model may describe a machine learning model configured to process one or more health history data objects associated with the visual representation of the target user and generate an associated health determination score. In some embodiments, the health history machine learning model may include a feature engineering layer configured to process the health history data object to infer features related to at least the age, gender, and one or more associated medical conditions for the target user depicted in the video stream data object. In some embodiments, a determined age may be represented as a numeric feature, gender may be represented as a one hot encoded value, and the health status and associated medical conditions may be represented as categorical values. In some embodiments, the health history machine learning model may be a natural language processing model. The health determination score may describe a disease contraction/transmission score for a target user as determined by a health history machine learning model in accordance with the health history data object for the target user.

In some embodiments, the health history machine learning model may process the health history data objects and classify any identified health conditions into a predefined category indicative of whether the associated health condition is known to or may increase the risk of severe illness should a particular disease be contracted. In some embodiments, medical condition categories may include a high risk category, a medium risk category, and/or a low risk category, where high risk category indicates that the target user depicted in the video stream data object has one or more medical conditions known to increase their associated risk of severe illness should the disease be contracted, and the medium risk category indicates that the target user depicted in the video stream data object has one or more medical conditions that may increase their associated risk of severe illness should the disease be contracted. The high risk and medium risk categories may each be associated with a set of predefined associated medical conditions, and the low risk category may indicate the absence of health conditions associated with increased risk for severe illness. The high risk and medium risk categories may each be associated with a set of predefined associated medical conditions. For example, the high risk category may include medical conditions such as cancer, kidney disease, heart conditions, chronic obstructive pulmonary disease, organ transplant, obese, pregnant, nursing, sickle cell disease, smoking, and type 2 diabetes. The medium risk category may include medical conditions such as asthma, cerebrovascular disease, cystic fibrosis, hypertension, weakened immune system, dementia, liver disease, overweight, pulmonary fibrosis, thalassemia, or type 1 diabetes.

In some embodiments, the number of health conditions associated with the high risk and medium risk category may be output. For example, if health history data object of the target user depicted in the video stream data object may be processed by the health history machine learning model, which may identify the target user depicted in the video stream data object has two medical conditions known to be high risk. In this case, the associated health determination score may indicate a 2 in the high risk category and 0 in the medium risk and low risk categories. In some embodiments, a binary value may be used to indicate whether the target user depicted in the video stream data object has one or more medical condition that fall into one of the predetermined categories. By way of continuing example, the same user with two medical conditions known to be high risk, may have an associated health determination score of 1 in the high risk category and 0 in the medium risk and low risk categories.

At step/operation 506, the predictive data analysis computing entity 106 updates the predicted disease score generated at step/operation 408 based at least in part on the health determination score using the logarithmic merger machine learning model. Similar to the step/operation described with respect to step/operation 408, the logarithmic merger machine learning model may update the predicted disease score, originally calculated based at least in part on the protective covering indication and the spatial proximity determination score, to include consideration the health determination score as well.

The logarithmic merger machine learning model may determine an associated age of the target user depicted in the video stream data object based at least in part on the health determination score generated by the health history machine learning model (e.g., OpenCV, Deep Learning, and Python). In some embodiments, the logarithmic merger machine learning model may be configured to determine a predetermined age category the target user belongs to. For example, the health determination score may indicate that the target user depicted in the video stream data object is 40 years old. Based at least in part on this health determination score, the logarithmic merger machine learning model may determine the target user belongs in the 40-49 age category. In some embodiments, each age category may be associated with a predetermined value indicative of a change in associated risk of severe illness if a disease is contracted. By way of continuing example, target users determined to belong to the 40-49 age category may have a three times higher associated risk score as compared to target users belonging to a 18-29 age category. As another example, target users determined to belong to a 5-17 age category may have a nine times lower associated risk score as compared to target users belonging to a 18-29 age category. The logarithmic merger machine learning model may update the predicted disease score associated with target user depicted in the video stream data object based the associated predetermined value for the age category the target user belongs to.

The logarithmic merger machine learning model may also determine if the target user depicted in the video stream data object has any medical conditions that are deemed to put the health of said target user at increased health risk should the target user contract the disease based at least in part on the health determination score generated by the health history machine learning model. The logarithmic merger machine learning model may be configured with predetermined values for each medical condition category, where the predetermined values are indicative of the amount to update the predicted disease score. By way of continuing the above-described example, if the health determination score indicates the target user depicted in the video stream data object has an associated medical condition belonging in the high risk category, the logarithmic merger machine learning model may update the predicted disease score by an associated predetermined amount. Similarly, if the health determination score indicates the target user depicted in the video stream data object has a medical condition belonging in the medium risk category and a medical condition belonging in the high risk category, the logarithmic merger machine learning model may update the predicted disease score by both the predetermined amount associated with the high risk category and the predetermined amount associated with the medium risk category. As another example, logarithmic merger machine learning model may be configured with multiple predetermined values for a single risk category based at least in part on the number of medical conditions associated with the category. For example, if a target user is determined to have two medical conditions in the high risk category, the logarithmic merger machine learning model may update the predicted disease score by a predetermined value associated with two high risk medical conditions.

In some embodiments, the logarithmic merger machine merger model may adjust the predefined predicted disease score threshold based at least in part on the health determination score of the target user depicted in the video stream data object. Prior to receiving the health determination score, the logarithmic merger machine learning model may have a predefined predicated disease score threshold, indicative of a maximum predicted disease score for an average target user before the target user is predicted to be at increased risk for contracting or transmitting a disease. However, certain populations of target user's (such as the elderly and individuals with certain medical conditions) are at greater health risk should they contract the disease. Therefore, a predicted disease score threshold that considers one or more medical conditions or an age of a target user may help prevent the target user from contracting the disease. Similar to the above, the logarithmic merger machine learning model may have predetermined predicted disease score threshold values associated with each age categories and each medical condition category. Based at least in part on these predetermined predicted disease score threshold values, the logarithmic merger machine learning model may update the predicted disease score threshold.

In some embodiments, step/operation 408 can also be performed in accordance with the process 408B that is depicted in FIG. 6. The process 408B that is depicted in FIG. 6 begins at step/operation 602 when the predictive data analysis computing entity 106 receives a video stream data object depicting a visual representation of a target user. Similar to the step/operation 402 described above, the video stream data object may be received from an external device, such as a video capture device configured with a camera and capable of electronically transmitting the video stream data object, where the video stream data object depicts a visual representation of a target user.

At step/operation 604, the predictive data analysis computing entity 106 processes the video stream data object using an age estimation machine learning model in order to generate an age prediction. An age estimation machine learning model may describe a machine learning model configured to process a visual representation of a target user depicted in the received video stream data object to generate an age estimation score. In some embodiments, the age estimation machine learning model may be trained using observed data to determine the estimated age of the target user. In some embodiments, the age estimation machine learning model may be trained to assign the target user an estimated age category amongst a set of predetermined age ranges. For example, the age estimation machine learning model may determine the visual representation of the target user belongs in a 40-49 age category. As another example, the age estimation machine learning model may determine the visual representation of the target user belongs in an 85 or older age category.

At step/operation 606, the predictive data analysis computing entity 106 updates the predicted disease score generated at step/operation 408 based at least in part on the age prediction using the logarithmic merger machine learning model. Similarly to the step/operation described with respect to step/operation 408, the logarithmic merger machine learning model may update the predicted disease score, originally calculated based at least in part on the protective covering indication and the spatial proximity determination score, to include consideration of the age prediction as well.

Similar to the step/operation performed in step/operation 506, in some embodiments, the logarithmic merger machine learning model updates the predicted disease score associated with the target user depicted in video stream data object based at least in part on the age determinations score. For example, the age prediction may indicate that the target user depicted in the video stream data object belongs to the 40-49 age category. In some embodiments, the predetermined age categories in the logarithmic merger machine learning model and the age estimation machine learning model are the same. In some embodiments, each age category may be associated with a predetermined value indicative of a change in associated risk of severe illness if a disease is contracted. The logarithmic merger machine learning model may update the predicted disease score associated with target user depicted in the video stream data object based at least in part on the associated predetermined value for the category the target user belongs to.

In some embodiments, step/operation 408 can also be performed in accordance with the process 408C that is depicted in FIG. 7. The process 408C that is depicted in FIG. 7 begins at step/operation 702 when the predictive data analysis computing entity 106 receives a video stream data object depicting a visual representation of a target user. Similar to the step/operation 402 described above, the video stream data object may be received from an external device (such as a video capture device capable of electronically transmitting the video stream data object) and depicts a visual representation of a target user.

At step/operation 704, the predictive data analysis computing entity 106 processes the video stream data object using an illness detection machine learning model in order to generate an illness observation indication. An illness detection machine learning model may describe a machine learning model configured to process a visual representation of a target user depicted in the received video stream data object to generate an illness observation indication that describes an inferred prediction about preexisting illnesses of the target user. In some embodiments, the illness detection machine learning model may be trained using observed visual pattern and auditory pattern data to determine if the visual representation of the target user is exhibiting symptoms indicative of illness.

In some embodiments, the illness detection machine learning model may be configured to detect any the visual illness patterns for a target user (e.g., certain gestures indicative of illness). For example, the illness detection machine learning model may detect visual illness patterns associated with sneezing, coughing, blowing his/her nose, and/or the like. In some embodiments, the illness detection machine learning model may be configured to detect auditory illness patterns indicative of illness. For example, the illness detection machine learning model may detect the auditory illness patterns indicating the visual representation of the target user is coughing, sneezing, and/or blowing his/her nose. By way of example, if the visual representation of the target user depicts that the target user raises his/her hand to cover his/her nose while sneezing, the illness detection model may detect the visual illness pattern and therefore classify the visual representation of the target user as exhibiting symptoms of illness. As another example, if the visual representation of the target user depicts that the target coughs, the illness detection machine learning model may detect the auditory illness pattern from the cough and therefore classify the visual representation of target user as exhibiting symptoms of illness.

At step/operation 706, the predictive data analysis computing entity 106 updates the predicted disease score generated at step/operation 408 based at least in part on the illness detection score using the logarithmic merger machine learning model. Similarly to the step/operation described with respect to step/operation 408, the logarithmic merger machine learning model may update the predicted disease score, originally calculated based at least in part on the protective covering indication and the spatial proximity determination score, to include consideration of the illness observation indication as well.

In some embodiments, if the illness observation indication associated with the visual representation of the target user indicates that the visual representation of the target user is exhibiting symptoms of illness, the predicted disease score is changed by a predetermined amount. For example, in instances when the visual representation of the target user is determined to have made a gesture indicative of a sneeze, the illness observation indication may be 1 as determined by the illness detection machine learning model. When updating the predicted disease score, logarithmic merger machine learning model may update the predicted disease score to increase the predicted disease score by a predefined amount (e.g., by 10 percentage points) due to the illness observation indication indicating the visual representation of the target user exhibiting symptoms of illness. As another example, in instances when the visual representation of the target user is determined not to have exhibited any signs of illness as determined by the illness detection machine learning model, the illness observation indication may be 0. In some embodiments, the logarithmic merger machine learning model may decrease the predicted disease score by a predetermined amount if the visual representation of the target user is found to not be exhibiting symptoms of illness.

In some embodiments, step/operation 408 can also be performed in accordance with the process 408D that is depicted in FIG. 8. The process 408D that is depicted in FIG. 8 begins at step/operation 802 when the predictive data analysis computing entity 106 receives a video stream data object depicting a visual representation of a target user. Similar to the step/operation 402 described above, the video stream data object may be received from an external device (such as a video capture device capable of electronically transmitting the video stream data object) and depicts a visual representation of a target user.

At step/operation 804, the predictive data analysis computing entity 106 processes the video stream data object using an environmental monitoring machine learning model in order to generate an environmental risk determination score. An environmental monitoring machine learning model may describe a machine learning model configured to process a surrounding environment of a visual representation of a target user depicted in the received video stream data object to generate an environmental risk determination score (e.g., an environmental risk determination score that is indicative of a disease risk factor associated with the target user as determined based at least in part on one or more inferred environmental conditions of the target user). In some embodiments, the environmental risk determination machine learning model may be trained using observed data describing features related the environment of the visual representation of the target user.

In some embodiments, the environmental monitoring machine learning model may be trained to detect one or more visual representations of individuals other than visual representation of the target user. For example, if a single target user is selected, detection of any other visual representations of individuals other than the visual representation of the target user may be used to generate features related to as environment of the visual representation of the target user. In some embodiments, the distance between one or more detected visual representation of individuals and the visual representation of the target individual may be detected and utilized by the environmental monitoring machine learning model. This determination may be performed in a similar manner as described with respect to step/operation 406 using the spatial proximity machine learning model, using a predefined face length and video capture device focal length, and by processing the video stream data object to estimate the number of pixels comprising the visual representation of the individuals face.

In some embodiments, the environmental monitoring machine learning model may be trained to determine if the visual representation of the target user is indoors or outdoors. In some embodiments, the location of the video capture device may include location determining aspects. For example, the video capture device may include outdoor or indoor positioning aspects, in accordance with aspects described with reference to external computing entity 102. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using GPS). The satellites may be a variety of different satellites, including LEO satellite systems, DOD satellite systems, the European Union Galileo positioning systems, the Chinese Compass navigation systems, Indian Regional Navigational satellite systems, and/or the like. This data can be collected using a variety of coordinate systems, such as the DD; DMS; UTM; UPS coordinate systems; and/or the like. Alternatively, the location information/data can be determined by triangulating the external device's position in connection with a variety of other systems, including cellular towers, Wi-Fi access points, and/or the like. Similarly, the external device may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, BLE transmitters, NFC transmitters, and/or the like. These indoor positioning aspects can be used in a variety of settings to determine the location of someone or something to within inches or centimeters. In some embodiments, the video capture device is stationary, such as when the digital capture device is a digital signage, such that the location of the video capture device is known. As such, the environmental monitoring machine learning model may associate a static variable indicative of whether the environment of the visual representation of the target user is indoors or outdoors.

At step/operation 806, the predictive data analysis computing entity 106 updates the predicted disease score generated at step/operation 408 based at least in part on the environmental risk determination score using the logarithmic merger machine learning model. Similarly to the step/operation described with respect to step/operation 408, the logarithmic merger machine learning model may update the predicted disease score, originally calculated based at least in part on the protective covering indication and the spatial proximity determination score, to include consideration of the environmental risk determination score as well.

In some embodiments, the logarithmic merger machine learning model may be configured to use a logarithmic algorithm with the environmental risk determination score to update the predicted disease score. For example, if the environmental risk determination score indicates one detected visual representation of an individual other than the visual representation of the target user, the distance between the visual representation of the individual and the visual representation of the target user may be indicated by the environmental risk determination score. The logarithmic merger machine learning model may use the environmental risk determination score indicative of the distance between the visual representation of the individual and the visual representation of the target user in the logarithmic algorithm to update the predicted disease score for the target user depicted in the video stream data object.

In some embodiments, the logarithmic merger machine learning model may be further configured to add a predetermined amount to the predicted disease score based at least in part on a determined location of a user. For example, if the visual representation of the target user is determined to be in an indoor environment, the predicted disease score associated with the target user may increase by 5 percentage points.

The operations associated with the above-described machine learning models associated with step/operation 408, including the health history machine learning model, the age estimation machine learning model, the illness detection machine learning model, and the environmental machine learning model may be performed in any order or may be performed simultaneously. In this way, an accurate real-time predicted disease score may be generated for the user by the logarithmic merger machine learning model.

Returning to FIG. 4, at step/operation 410, the predictive data analysis computing entity 106 provides an augmented reality video stream data object configured to be presented to at least the target user via an external computing entity 102. In some embodiments, the external computing entity 102 that receives the augmented reality video stream data object comprises the video capture device that transmits the video stream data object. The augmented reality video stream data object describes audiovisual data received from the video stream data object along with one or more embedded, overlaid, and/or the like augmented reality user interface elements. In some embodiments, the augmented reality video stream data object comprises a visual representation of the target user and a data object indicating the depicted target user's associated predicted disease score as determined by the logarithmic merger machine learning model.

In some embodiments, the augmented reality video stream data object may include an embedded bounding box. The bounding box may be a color-coded bounding box that is centered about the visual representation of the target user's face. The color of the color-coded bounding box may indicate whether the determined predicted disease score associated with the depicted target user is above or below an associated threshold predicted disease score. For example, if a predicted disease score associated with the depiction of the target user is below the threshold predicted disease score, the bounding box may be green. As another example, if a predicted disease score associated with the depiction of the target user is at or above the threshold predicted disease score, the bounding box may be red.

In some embodiments, the augmented reality video stream data object may include an embedded recommendation element, where the recommendation element displays one or more recommended actions that the target user depicted by the video stream data object may take to reduce his/her associated predicted disease score as generated by in step/operation 408 by the logarithmic merger machine learning. In this way, the augmented reality video stream data object displays one or more actions the depicted target user may take to reduce his/her disease score.

Figure 9B:
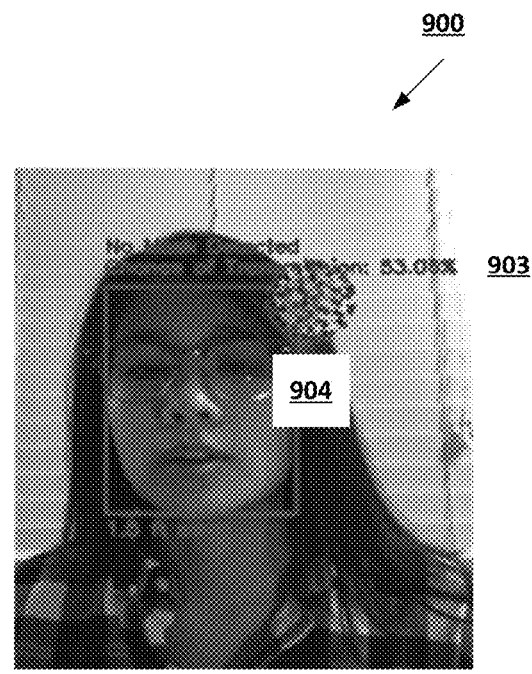

An operational example of an augmented reality video stream data object 900 is depicted in FIGS. 9A and 9B. As depicted in FIGS. 9A and 9B, the augmented reality video stream data object 900 depicts the audiovisual data received from the video stream data object along with one or more embedded augmented reality user interface elements. As depicted in FIG. 9A, the augmented reality video stream data object 900 includes the predicted disease score 901. As further depicted in FIG. 9A, the augmented reality video stream data object 900 also relays information related to the determined protective covering indication and proximity detection score for the visual representation of the target user as determined by the covering detection machine learning model and spatial proximity machine learning model, respectively. In this instance, the predicted disease score 901 associated with the target user is determined to be 19.74%. The green bounding box 902 centered about the visual representation of the target user's face indicates this predicted disease score falls below a threshold predicted disease score determined for the visual representation of the target user. Although not shown here, other data objects, such as data objects indicative of a health determination score, age prediction, illness observation indication, or environmental risk determination score may be embedded in the augmented reality video stream data object.

As depicted in FIG. 9B, the augmented reality video stream data object 900 depicts the same target user visual representation and also, the same determined proximity detection score of 1.5 feet. However, the protective covering machine learning model has determined that the visual representation of the target user is not wearing a mask. As such, the predicted disease score 903 associated with the visual representation of the target user has increased to 53.06%. Moreover, the bounding box 904 centered about the visual representation of the target user's face is now red, indicating the associated predicted disease score is above a threshold predicted disease score determined for the visual representation for the target user. Although not shown here, a recommendation data object may be embedded in the augmented reality video stream data object such that the target user depicted in the video stream data object is recommended actions to take to reduce his/her corresponding predicted disease score.

In some embodiments, based at least in part on the predicted disease score associated with the target user depicted by the video stream data object, one or more actions may occur to prevent an increased risk of disease transmission. For example, if the predicted disease score associated with the target user depicted by the video stream data object is above a preconfigured threshold predicted disease score, the target user associated with the predicted disease score may be denied entry into a particular building and/or entrance. The target user may be denied entry for as long as their associated predicted disease score is above the preconfigured threshold. Additionally or alternatively, in some embodiments, the one or more actions may comprise generating and sending an alert to one or more associated computing entities and/or associated user accounts such that the alert notifies the designated recipient that the target user depicted by the video stream data object is above the preconfigured threshold predicted disease score. In this way, the recipient may be alerted to the potential increased risk of disease transmission and therefore take one or more corresponding actions including but not limited to turning the associated target user away, offering the associated target user a mask if they are not already wearing one, or alerting one or more authorities, such as onsite security, to the situation.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for dynamically generating a predicted disease score for a video stream data object depicting a visual representation of a target user, the computer-implemented method comprising:
    receiving, using one or more processors, a video stream data object, wherein the video stream data object (a) comprises sequential image data generated by a video capture device, and (b) depicts a visual representation of a target user;
    generating, using the one or more processors and by using a covering detection machine learning model, a protective covering indication with respect to the visual representation of the target user depicted in the video stream data object, wherein the covering detection machine learning model is configured to process at least the video stream data object to generate the protective covering indication;
    generating, using the one or more processors and by using a spatial proximity machine learning model, a spatial proximity determination score with respect to the visual representation of the target user depicted in the video stream data object, wherein the spatial proximity machine learning model is configured to process at least the video stream data object to generate the spatial proximity determination score;
    generating, using the one or more processors and by using a logarithmic merger machine learning model, a predicted disease score, wherein the logarithmic merger machine learning model is configured to process at least the protective covering indication and spatial proximity determination score to generate the predicted disease score; and
    generating and providing an augmented reality video stream data object for presentation to an end user, wherein the augmented reality video stream data object comprises (a) the visual representation of the target user, and (b) the predicted disease score.

2. The computer-implemented method of claim 1, further comprising:
    determining, using the one or more processors and by using the logarithmic merger machine learning mode, one or more recommended actions for the user to take, wherein the one or more recommended actions describe one or more actions for the target user depicted in the video stream data object to take to reduce the predicted disease score, and
    wherein the one or more recommended actions are determined based at least in part on the protective covering indication and the spatial proximity determination score.

3. The computer-implemented method of claim 1, further comprising:
    receiving, using the one or more processors, a health history data object pertaining to the target user depicted in the video stream data object;
    generating, using the one or more processors and by using a health history machine learning model, a health determination score with respect to at least the visual representation of the target user depicted in the video stream data object, wherein the health history machine learning model is configured to process at least the health history data object to generate the health determination score; and
    updating, using the one or more processors and by using the logarithmic merger machine learning model, the predicted disease score associated with the target user, wherein the logarithmic merger machine learning model is provided at least the health determination score, the protective covering indication, and the spatial proximity determination score to update the predicted disease score.

4. The computer-implemented method of claim 1, further comprising:
    generating, using the one or more processors and by using an age estimation machine learning model, an age prediction with respect to at least the visual representation of the target user, wherein the age estimation machine learning model is configured to process at least the video stream data object to generate the age prediction;
    updating, using the one or more processors and by using the logarithmic merger machine learning model, the predicted disease score associated with the target user, wherein the logarithmic merger machine learning model is provided at least the age prediction, the protective covering indication, and the spatial proximity determination score to update the predicted disease score.

5. The computer-implemented method of claim 1, further comprising:
    generating, using the one or more processors and by using an illness detection machine learning model, an illness observation indication based at least on one or more visual illness patterns or one or more auditory illness patterns from the video stream data object, wherein the illness detection machine learning model is configured to process at least the video stream data object to generate the illness observation indication;
    updating, using the one or more processors and by using the logarithmic merger machine learning model, the predicted disease score associated with the target user, wherein the logarithmic merger machine learning model is provided at least the illness observation indication, the protective covering indication, and the spatial proximity determination score to update the predicted disease score.

6. The computer-implemented method of claim 1, further comprising:
    generating, using the one or more processors and by using an environmental monitoring machine learning model, an environmental risk determination score for an environment of the target user, wherein the environmental monitoring machine learning model is configured to process at least the video stream data object to generate the environmental risk determination score;
    updating, using the one or more processors and by using a logarithmic merger machine learning model, the predicted disease score associated with the target user, wherein the logarithmic merger machine learning model is provided at least the environmental risk determination score, the protective covering indication, and the spatial proximity determination score to update the predicted disease score.

7. The computer-implemented method of claim 1, wherein the augmented reality video stream data object is further configured to modify the video stream data object, wherein modifying the video stream data object comprises embedding a bounding box data object centered about a detected facial point of the visual representation of the target user, and wherein the bounding box is color-coded to indicate whether the generated predicted disease score satisfies a predefined predicted disease score threshold.

8. The computer-implemented method of claim 1, further comprising:
generating, using the one or more processors and by using the logarithmic merger machine learning model, a threshold predicted disease score for the visual representation of the target user.

9. An apparatus for dynamically generating a predicted disease score for a video stream data object depicting a visual representation of a target user, the apparatus comprising at least one processor and at least one memory including program code, the at least one memory and the program code configured to, with the processor, cause the apparatus to at least:
receive a video stream data object, wherein the video stream data object (a) comprises sequential image data generated by a video capture device, and (b) depicts a visual representation of a target user;
generate, using a covering detection machine learning model, a protective covering indication with respect to the visual representation of the target user depicted in the video stream data object, wherein the covering detection machine learning model is configured to process at least the video stream data object to generate the protective covering indication;
generate, using a spatial proximity machine learning model, a spatial proximity determination score with respect to the visual representation of the target user depicted in the video stream data object, wherein the spatial proximity machine learning model is configured to process at least the video stream data object to generate the spatial proximity determination score;
generate, using a logarithmic merger machine learning model, a predicted disease score, wherein the logarithmic merger machine learning model is configured to process at least the protective covering indication and spatial proximity determination score to generate the predicted disease score; and
provide an augmented reality video stream data object for presentation to an end user, wherein the augmented reality video stream data object comprises (a) the visual representation of the target user, and (b) the predicted disease score.

10. The apparatus of claim 9, further configured to:
determine, using one or more processors and by using the logarithmic merger machine learning mode, one or more recommended actions for the user to take,
wherein the one or more recommended actions describe one or more actions for the target user to take to reduce the predicted disease score, and
wherein the one or more recommended actions are determined based at least in part on the protective covering indication and the spatial proximity determination score.

11. The apparatus of claim 9, further configured to:
receive a health history data object pertaining to the target user;
generate, using a health history machine learning model, a health determination score with respect to at least the visual representation of the target user, wherein the health history machine learning model is configured to process at least the health history data object to generate the health determination score; and
update, using the logarithmic merger machine learning model, the predicted disease score associated with the target user, wherein the logarithmic merger machine learning model is provided at least the health determination score, protective covering indication and spatial proximity determination score to update the predicted disease score.

12. The apparatus of claim 9, further configured to:
generate, using an age estimation machine learning model, an age prediction with respect to at least the visual representation of the target user, wherein the age estimation machine learning model is configured to process at least the video stream data object to generate the age prediction;
update, using the logarithmic merger machine learning model, the predicted disease score associated with the target user, wherein the logarithmic merger machine learning model is provided at least the age prediction, protective covering indication and spatial proximity determination score to update the predicted disease score.

13. The apparatus of claim 9, further configured to:
generate, using an illness detection machine learning model, an illness observation indication based at least on one or more visual illness patterns or one or more auditory illness patterns from the video stream data object, wherein the illness detection machine learning model is configured to process at least the video stream data object to generate the illness observation indication;
update, using the logarithmic merger machine learning model, the predicted disease score associated with the target user, wherein the logarithmic merger machine learning model is provided at least the illness observation indication, protective covering indication and spatial proximity determination score to update the predicted disease score.

14. The apparatus of claim 9, further configured to:
generate, using an environmental monitoring machine learning model, an environmental risk determination score for an environment of the target user, wherein the environmental monitoring machine learning model is configured to process at least the video stream data object to generate the environmental risk determination score;
update, using a logarithmic merger machine learning model, the predicted disease score associated with the target user, wherein the logarithmic merger machine learning model is configured to process at least the environmental risk determination score, protective covering indication and spatial proximity determination score to update the predicted disease score.

15. The apparatus of claim 9, wherein the augmented reality video stream data object is further configured to modify the video stream data object, wherein the modifying the video stream data object comprises embedding a bounding box data object centered about a detected facial point of the visual representation of the target user, and wherein the bounding box is color-coded to indicate whether the generated predicted disease score satisfies a predefined predicted disease score threshold.

16. The apparatus of claim 9, further configured to, generate, using the logarithmic merger machine learning model, a threshold predicted disease score for the visual representation of the target user.

17. A computer program product for dynamically generating a predicted disease score for a video stream data object depicting a visual representation of a target user, the computer program product comprising at least one non-transitory computer-readable storage medium having computer-readable program code portions stored therein, the computer-readable program code portions configured to:
- receive a video stream data object, wherein the video stream data object (a) comprises sequential image data generated by a video capture device, and (b) depicts a visual representation of a target user;
- generate, using a covering detection machine learning model, a protective covering indication with respect to the visual representation of the target user, wherein the covering detection machine learning model is configured to process at least the video stream data object to generate the protective covering indication;
- generate, using a spatial proximity machine learning model, a spatial proximity determination score with respect to the visual representation of the target user depicted in the video stream data object, wherein the spatial proximity machine learning model is configured to process at least the video stream data object to generate the spatial proximity determination score;
- generate, using a logarithmic merger machine learning model, a predicted disease score, wherein the logarithmic merger machine learning model is configured to process at least the protective covering indication and spatial proximity determination score to generate the predicted disease score; and
- provide an augmented reality video stream data object for presentation to an end user, wherein the augmented reality video stream data object comprises (a) the visual representation of the target user, and (b) the predicted disease score.

18. The computer program product of claim 17, further configured to:
- determine, using logarithmic merger machine learning model, one or more recommended actions for the user to take,
    - wherein the one or more recommended actions describe one or more actions for the target user to take to reduce the predicted disease score, and
    - wherein the one or more recommended actions are determined based at least in part on the protective covering indication and the spatial proximity determination score.

19. The computer program product of claim 17, wherein the augmented reality video stream data object is further configured to modify the video stream data object, wherein the modifying the video stream data object comprises embedding a bounding box data object centered about a detected facial point of the visual representation of the target user, and wherein the bounding box is color-coded to indicate whether the generated predicted disease score satisfies a predefined predicted disease score threshold.

20. The computer program product of claim 17, further configured to, generate, using the logarithmic merger machine learning model, a threshold predicted disease score for the visual representation of the target user.

* * * * *

UNITED STATES PATENT AND TRADEMARK OFFICE
CERTIFICATE OF CORRECTION

| | |
|---|---|
| PATENT NO. | : 11,594,335 B2 |
| APPLICATION NO. | : 17/197909 |
| DATED | : February 28, 2023 |
| INVENTOR(S) | : Geo Min et al. |

It is certified that error appears in the above-identified patent and that said Letters Patent is hereby corrected as shown below:

In the Claims

In Column 33, Line 14, Claim 17, delete "user, wherein" and insert -- user depicted in the video stream data object, wherein --, therefor.

Signed and Sealed this
Sixteenth Day of May, 2023

Katherine Kelly Vidal
*Director of the United States Patent and Trademark Office*